United States Patent
Parthasaradhi Reddy et al.

(10) Patent No.: US 7,834,027 B2
(45) Date of Patent: Nov. 16, 2010

(54) GEMIFLOXACIN PROCESS AND POLYMORPHS

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN)

(73) Assignee: Hetero Drugs Limited, Hyderabad (IN)

( * ) Notice: Subject to any disclaimer, the term of this patent is extended or adjusted under 35 U.S.C. 154(b) by 45 days.

(21) Appl. No.: 11/570,173

(22) PCT Filed: Jun. 15, 2005

(86) PCT No.: PCT/IN2005/000200

§ 371 (c)(1),
(2), (4) Date: Dec. 7, 2006

(87) PCT Pub. No.: WO2006/134608

PCT Pub. Date: Dec. 21, 2006

(65) Prior Publication Data

US 2008/0293760 A1   Nov. 27, 2008

(30) Foreign Application Priority Data

Jun. 15, 2005   (WO) .................. PCT/IN05/00200

(51) Int. Cl.
*C07D 471/04* (2006.01)
*A61K 31/4375* (2006.01)
*A61P 31/04* (2006.01)

(52) U.S. Cl. ..................... 514/300; 546/123
(58) Field of Classification Search ................. 514/300; 546/123
See application file for complete search history.

(56) References Cited

U.S. PATENT DOCUMENTS

| 5,633,262 A | 5/1997 | Hong et al. |
| 5,869,670 A | 2/1999 | Hong et al. |
| 6,818,771 B1 | 11/2004 | Hayes et al. |
| 2002/0032216 A1* | 3/2002 | Kim et al. ................... 514/300 |

FOREIGN PATENT DOCUMENTS

| WO | 98/42705 | * 10/1998 |
| WO | WO9842705 A1 | 10/1998 |
| WO | WO0118002 A1 | 3/2001 |
| WO | 03/011450 | * 2/2003 |

OTHER PUBLICATIONS

International Search Report and the Written Opinion of the International Searching Authority, or the Declaration Dated Mar. 8, 2006.

* cited by examiner

*Primary Examiner*—D. Margaret Seaman
*Assistant Examiner*—Niloofar Rahmani
(74) *Attorney, Agent, or Firm*—Caesar, Rivise, Bernstein, Cohen & Pokotilow, Ltd.

(57) ABSTRACT

The present invention provides a novel process for the preparation of gemifloxacin and its pharmaceutically acceptable acid addition salts in high yield. The present invention also relates to novel polymorphs of gemifloxacin free base and its hydrates to the processes for their preparation and to pharmaceutical compositions comprising them. The present invention also relates to infusion solutions of gemifloxacin and to processes for their preparation. Thus, 7-chloro-1-cyclopropyl-6-fluoro-4-oxo-1,4-dihydro-1, 8-naphthyridine-3-carboxylic acid is reacted with a mixture of acetic anhydride, acetic acid and boric acid to give borane compound, which is then treated with 4-Aminomethyl-3-methoxyimino-pyrrolidinium dimethanesulfonate in presence of triethylamine, followed by treatment with 3.5% sodium hydroxide solution to give gemifloxacin free base.

4 Claims, 2 Drawing Sheets

GEMIFLOXACIN PROCESS AND POLYMORPHS

FIELD OF THE INVENTION

The present invention provides a novel process for the preparation of gemifloxacin and its pharmaceutically acceptable acid addition salts in high yield. The present invention also relates to novel polymorphs of gemifloxacin free base and its hydrates, to the processes for their preparation and to pharmaceutical compositions comprising them. The present invention also relates to infusion solutions of gemifloxacin and to processes for their preparation.

BACKGROUND OF THE INVENTION

U.S. Pat. No. 5,633,262 disclosed a novel quinoline(naphthyridine) carboxylic acid derivatives and pharmaceutically acceptable salts thereof. These compounds are antibacterial agents. Among them gemifloxacin, chemically 7-[3-(Aminomethyl)-4-(methoxyimino)-1-prrolidinyl]-1-cyclopropyl-6-fluoro-1,4-dihydro-4-oxo-1,8-naphthyridine-3-carboxylic acid is a third generation fluorinated quinolone antibacterial agent. Gemifloxacin is represented by the following structure:

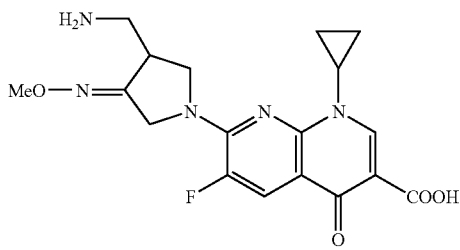

Processes for the preparations of gemifloxacin and related compounds were disclosed in U.S. Pat. No. 5,633,262 and PCT Patent Publication No. WO 01/18002 A1.

One object of the present invention is to provide a novel process for preparing gemifloxacin and pharmaceutically acceptable acid addition salts of gemifloxacin in high yield using novel intermediates.

Another object of the present invention is to provide a process for the preparation of amorphous gemifloxacin.

Another object of the present invention is to provide novel hydrates of gemifloxacin, processes for preparing them and pharmaceutical compositions comprising them.

Another object of the present invention is to provide a novel crystalline gemifloxacin lactic acid salt, process for preparing it and a pharmaceutical composition comprising it.

Another object of the present invention is to provide a novel crystalline gemifloxacin formic acid salt, process for preparing it and a pharmaceutical composition comprising it.

Another object of the present invention is to provide a process for the preparation of infusion solutions of gemifloxacin.

DETAILED DESCRIPTION OF THE INVENTION

According to one aspect of the present invention, there is provided a novel process for preparing gemifloxacin of the formula I:

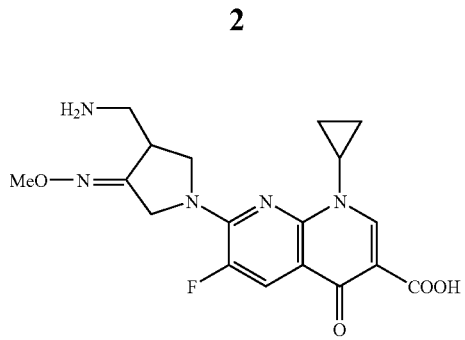

or a pharmaceutically acceptable salt thereof:

which comprises:

a) reacting 7-chloro-1-cyclopropyl-6-fluoro-4-oxo-1,4-dihydro-1,8-naphthyridine-3-carboxylic acid of the formula II:

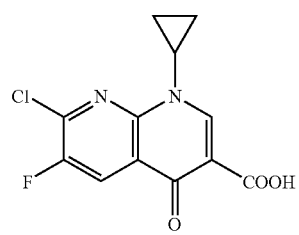

with boric acid of the formula III:

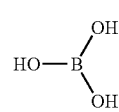

in the presence of acetic anhydride and acetic acid to give a borane compound of the formula IV:

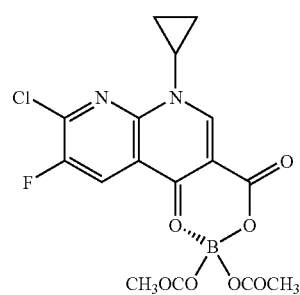

b) reacting the borane compound of the formula IV with 4-aminomethyl-3-methoxyimino-pyrrolidine of the formula V:

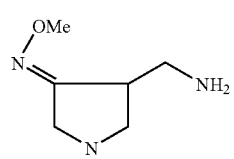

to give the compound of the formula VI:

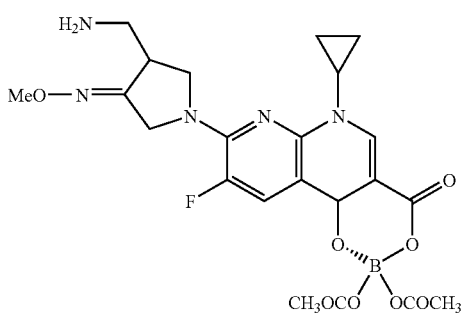

VI c) treating the compound of formula VI with an alkaline metal hydroxide, carbonate or bicarbonate to obtain gemifloxacin of the formula I and optionally converting the gemifloxacin formed into a pharmaceutically acceptable acid addition salt of gemifloxacin.

Borane compounds of the formulas IV and VI are novel and form part of the invention.

Preferably the reaction in step (a) is carried out at about 30° C. to the reflux temperature, more preferably at about 80° C. to the reflux temperature, and still more preferably at the reflux temperature.

Preferably, the borane compound of the formula IV formed is isolated as a solid by conventional means.

Preferably the reaction in step (b) is carried out at about 15-100° C., more preferably at about 30-80° C. and still more preferably at about 50-60° C.

Preferably the reaction in step (b) is carried out in a solvent selected from hydrocarbon solvents such as n-hexane, n-heptane and cyclohexane; chlorinated hydrocarbon solvents such as methylene chloride, ethylene chloride and chloroform, acetonitrile, tetrahydrofuran, 1,4-dioxane and a mixture thereof. The more preferable solvent is acetonitrile.

The compound of the formula V in step (b) may be used as a free base or as an acid addition salt form. If the compound of formula V is used as an acid addition salt, it is preferred to convert the salt to the free base before reacting it with the compound of the formula IV.

The preferred alkaline metal hydroxides used in step(c) are sodium hydroxide or potassium hydroxide; the preferred alkaline metal carbonate is sodium carbonate or potassium carbonate; and the preferred alkaline metal bicarbonate is sodium bicarbonate or potassium bicarbonate. The more preferable alkaline metal hydroxide is aqueous sodium hydroxide.

The compounds of formulae II and V are known and can be obtained from known procedures.

According to another aspect of the present invention, there is provided a process for the preparation of amorphous gemifloxacin, which comprises:
a) preparing a solution of gemifloxacin in dimethyl formamide or methylene chloride; and
b) isolating amorphous gemifloxacin from the solution.

The amorphous gemifloxacin is characterized by having broad X-ray diffraction spectrum as in FIG. 1.

The isolation may be initiated by a method usually known in the art such as cooling, seeding, partial removal of the solvent from the solution, addition of precipitating solvent or a combination thereof.

Preferably, isolation may be carried out by cooling or by using a precipitating solvent to obtain amorphous gemifloxacin. A typical X-ray diffraction spectrum of amorphous gemifloxacin is shown in FIG. 1.

According to another aspect of the present invention, there is provided a novel gemifloxacin hemihydrate.

According to another aspect of the present invention, a process is provided for the preparation of gemifloxacin hemihydrate, which comprises drying wet gemifloxacin at 40-100° C., preferably at 50-70° C. until the water content is reduced to 1.8-2.4% by weight. The control on the drying is required for the product not to be contaminated with other hydrate forms of gemifloxacin or anhydrous gemifloxacin.

According to another aspect of the present invention, there is provided a novel crystalline gemifloxacin monohydrate.

According to another aspect of the present invention, a process is provided for the preparation of gemifloxacin monohydrate, which comprises drying wet gemifloxacin at 40-100° C., preferably at 50-70° C. until the water content is reduced to 4.0-5.0% by weight. The control on the drying is required for the product not to be contaminated with other hydrate forms of gemifloxacin or anhydrous gemifloxacin.

According to another aspect of the present invention, a process is provided for the preparation of gemifloxacin sesquihydrate, which comprises drying wet gemifloxacin at 40-100° C., preferably at 50-70° C. until the water content is reduced to 5.8-6.5% by weight. The control on the drying is required for the product not to be contaminated with other hydrate forms of gemifloxacin or anhydride gemifloxacin.

The gemifloxacin hemihydrate, gemifloxacin monohydrate, gemifloxacin sesquihydrate may be converted to amorphous gemifloxacin using the hydrates as starting materials in the process for preparing amorphous gemifloxacin.

The wet gemifloxacin may be obtained by crystallizing gemifloxacin from an aqueous medium.

According to another aspect of the present invention, there is provided a novel crystalline form of gemifloxacin lactic acid salt, designated as gemifloxacin lactate, characterized by an x-ray powder diffraction spectrum having peaks expressed as 2θ at about 7.4, 7.7, 8.2, 9.1, 12.4, 18.5, 19.8, 23.6, 25.7 and 26.8 degrees. FIG. 2 shows a typical X-ray powder diffraction spectrum of gemifloxacin lactate.

According to another aspect of the present invention, a process is provided for the preparation of gemifloxacin lactate, which comprises contacting gemifloxacin with lactic acid. Preferably lactic acid or a solution of lactic acid is added to a solution of gemifloxacin. Gemifloxacin lactate may be isolated as a crystalline solid by conventional means.

The solvent used for preparing the solution of gemifloxacin is selected from the group consisting of chlorinated hydrocarbon solvents such as methylene chloride, ethylene chloride and chloroform, alcoholic solvents such as methanol, ethanol, isopropyl alcohol, tert-butyl alcohol and a mixture thereof. the more preferred solvents are methylene chloride, ethanol and a mixture thereof.

According to another aspect of the present invention, there is provided a novel crystalline form of gemifloxacin formic salt, designated as gemifloxacin formate.

According to another aspect of the present invention, a process is provided for the preparation of gemifloxacin formate, which comprises contacting gemifloxacin with formic acid. Preferably formic acid or a solution of formic acid is added to a solution of gemifloxacin. Gemifloxacin formate may be isolated as a crystalline solid by conventional means.

The solvent used for preparing the solution of gemifloxacin is selected from the group consisting of chlorinated hydrocarbon solvents such as methylene chloride, ethylene chloride and chloroform, alcoholic solvents such as methanol, ethanol, isopropyl alcohol and tert-butyl alcohol and a mixture thereof. The more preferred solvent is methylene chloride, ethanol and a mixture thereof.

The novel gemifloxacin hydrates may be used in pharmaceutical preparations. The pharmaceutical applications of gemifloxacin and its salts are described in U.S. Pat. No. 5,633,262 and PCT patent publication No. WO 01/18002 A1, which are incorporated herein by reference.

According to another aspect of the present invention there is provided a pharmaceutical composition comprising crystalline gemifloxacin hemihydrate and a pharmaceutically acceptable carrier.

According to another aspect of the present invention there is provided a pharmaceutical composition comprising crystalline gemifloxacin monohydate and a pharmaceutically acceptable carrier.

According to another aspect of the present invention there is provided a pharmaceutical composition comprising crystalline gemifloxacin sesquihydate and a pharmaceutically acceptable carrier.

According to another aspect of the present invention there is provided a pharmaceutical composition comprising crystalline gemifloxacin lactate and a pharmaceutically acceptable carrier.

According to another aspect of the present invention there is provided a pharmaceutical composition comprising crystalline gemifloxacin formate and a pharmaceutically acceptable carrier.

According to another aspect of the present invention, there is provided infusion solutions of gemifloxacin which contain 0.015 to 0.5 gm of gemifloxacin per 100 ml of aqueous solution and an amount of a physiologically tolerated acid which suffices to dissolve the gemifloxacin and to stabilize the solution and, where appropriate, customary formulating auxiliaries.

Preferably, the infusion solutions contain an amount of physiologically tolerated acid, which suffices to dissolve the gemifloxacin and to stabilize the solution, of one or more acid(s) from the group comprising hydrochloric acid, methanesulfonic acid, propionic acid, succinic acid, glutaric acid, citric acid, fumaric acid, maleic acid, tartaric acid, glutamic acid, gluconic acid, glucuronic acid, galacturonic acid, ascorbic acid, phosphoric acid, nitric acid, acetic acid, maleic acid, L-aspartic acid and lactic acid.

Preferable physiologically tolerated acids are lactic acid, hydrochloric acid or a mixture thereof. The more preferable physiologically tolerated acid is lactic acid.

More preferably, the infusion solutions which contain 0.015 to 0.5 gm of the gemifloxacin per 100 ml of aqueous solution and, depending on the gemifloxacin concentration, up to 5.0 moles, in particular 0.9 to 5.0 moles, and particularly 1.04 to 2.20 moles, relative to 1 mole of gemifloxacin, of one or more physiologically tolerated acids, and where several acids are present their total content does not exceed the amount of 5.0 moles, relative to 1 mole of gemifloxacin.

The infusion solutions according to the invention have a pH of 3.0 to 5.2. pH values from 3.6 to 4.7 and 3.9 to 4.5 are preferred. pH values in the range from 4.1 to 4.3 are very particularly preferred.

The particularly preferable infusion solution of gemifloxacin which, apart from gemifloxacin, water and other formulating auxiliaries, contain, depending on the amount of gemifloxacin, 0.99 to 1.50 moles, preferably 1.04 to 1.40 moles of lactic acid and 0.0to 0.80 moles of hydrochloric acid (in each case relative to 1 mole of gemifloxacin), and, relative to 100 ml of solution, 0.6 to 2.2 g of NaCl, preferably 0.75 to 1.20 gm, in particular 0.85 to 0.95 g of NaCl. The solutions thus obtained have osmolalities which differ according to the amount of sodium chloride and gemifloxacin concentration. The osmolalities relating to the amounts of sodium chloride listed above are 0.2 to 0.7, 0.26to 0.39 and 0.28 to 0.32 Osm/Kg of solution respectively. Corresponding values can also be adjusted using other isotonicizing agents or mixtures thereof, as indicated above. Depending on the gemifloxacin and acid concentration, small differences from these osmolalities are perfectly possible.

The infusion solutions according to the invention can be in the form of dosage units, suitable for infusion, with removable contents of 40 to 600 ml, preferably 50 to 120 ml.

According to another aspect of the present invention, a process is provided for the preparation of infusion solutions, which comprises mixing a suitable amount of the gemifloxacin, where appropriate in the form of a salt, such as an alkali metal or alkaline earth metal salt or addition salt, of a hydrate or of a hydrate of the salt, or in the form of mixtures of these salts or hydrates, with the amount of a physiologically tolerated acid or of a mixture of several physiologically tolerated acids which, in relation to the amount which just suffices to dissolve the gemifloxacin or its salts or hydrates, represents an excess preventing separation out of the gemifloxacin, adding, where appropriate, formulating auxiliaries, and making up with water or a customary infusion vehicle solutions in such a manner that the concentration of the gemifloxacin is adjusted to the range from 0.015 to 0.5 gm.

Figure 1:
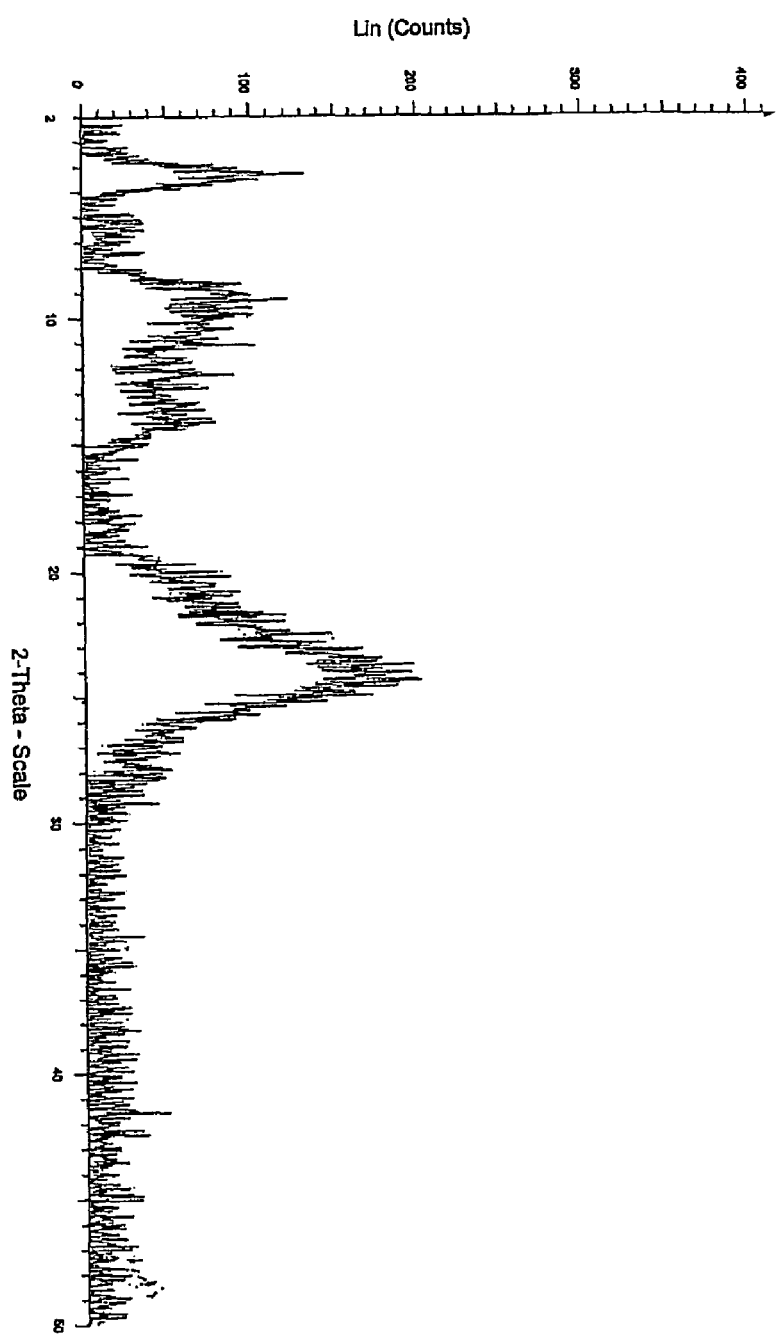
FIG. 1 shows typical X-ray powder diffraction spectrum of amorphous gemifloxacin.
Figure 2:
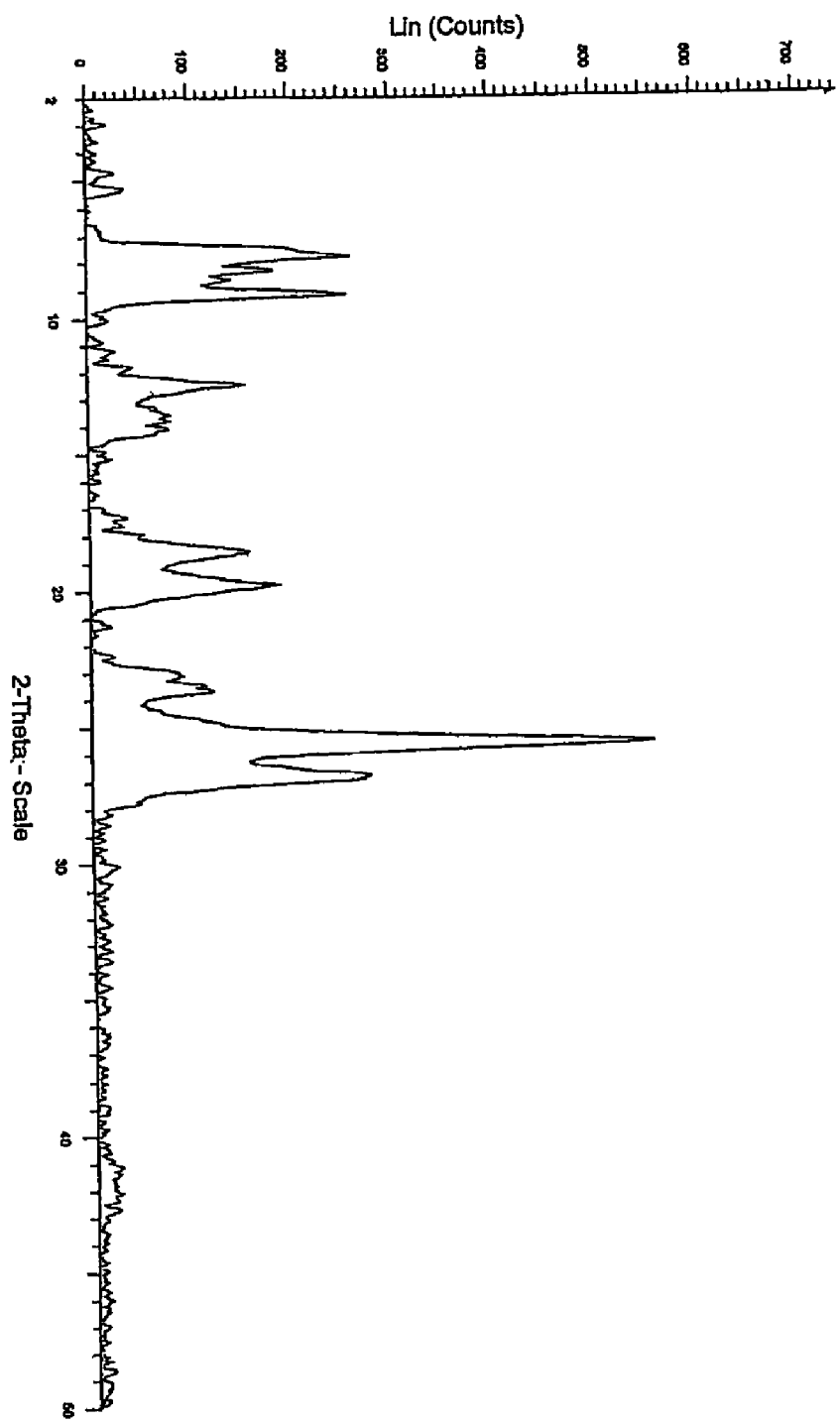
FIG. 2 shows typical X-ray powder diffraction spectrum of crystalline gemifloxacin lactate.

X-Ray powder diffraction spectrum was measured on a Bruker axs D8 advance x-ray powder diffractometer having a Copper-Kα radiation. Approximately 1 gm of sample was gently flattened on a sample holder and scanned from 2 to 50 degrees two-theta, at 0.03 degrees two-theta per step and a step time of 0.5 seconds. The sample was simply placed on the sample holder. The sample was rotated at 30 rpm at a voltage 40 KV and current 35 mA.

The invention will now be further described by the following examples, which are illustrative rather than limiting.

EXAMPLE 1

Acetic anhydride (35.5 ml) and acetic acid (16.5 ml) are added to boric acid (3.5gm), heated to reflux and then the contents are stirred for 3 hours at the same temperature. 7-Chloro-1-cyclopropyl-6-fluoro-4-oxo-1,4-dihydro-1,8-naphthyridine-3-carboxylic acid (27 gm) is added to the reaction mass and refluxed for 2 hours. Then toluene (200 ml) is added, cooled to 25-30° C. and distilled off the solvent under vacuum. Again toluene (200 ml) is added to the reaction mass, cooled to 5-10° C. and the separated solid is filtered and dried to give 38 gm of borane compound of the formula IV (HPLC Purity: 90%).

To the suspension of 4-Aminomethyl-3-methoxyimino-pyrrolidinium dimethanesulfonate (63.5 gm) in acetonitrile (125 ml) is added triethylamine (75 gm) and stirred for 30 minutes at 25-30° C. and then added borane compound (obtained above) to the contents. The contents are heated to 50-60° C. and stirred for 4 hours at the same temperature. Then the solvent was distilled off under reduced pressure, then cooled to 25-1 30° C., water (350 ml) was added and stirred for 10 minutes at 25-30° C. The compound was filtered and washed with water (50 ml). To the compound acetonitrile (100 ml) and 3.5% sodium hydroxide solution (250 ml) are added and stirred for 1 hour to form a clear solution. Then the pH of the solution is adjusted to 3.4 with 1N hydrochloric acid (25 ml) and the separated solid is stirred for 15 minutes. The material was filtered and washed with water (60 ml) to obtain wet gemifloxacin (HPLC purity: 99.8%).

The wet gemifloxacin was dried at 50-55° C. to constant weight to obtain 31.6gm anhydride gemifloxacin free base (HPLC Purity: 99.7%).

EXAMPLE 2

Anhydride gemifloxacin free base (10 gm, obtained in example 1) is added to dimethylformamide (300 ml) at 25-35° C., the contents are heated to 75-80° C. and stirred for 1 hours at the same temperature to form a clear solution. The reaction mass is cooled to 25-35° C. Then the separated solid is filtered, washed with diisopropyl ether (50 ml) and dried at 50-55° C. to give 5.2 gm of amorphous gemifloxacin free base (HPLC Purity: 99.92%).

EXAMPLE 3

Gemifloxacin free base (3 gm) is added to methylene dichloride (450 ml) and stirred for 20 minutes at the 25-35° C. to form a clear solution. Then added diisopropyl ether (900 ml) and stirred for 1 hour at the same temperature. The reaction mass is cooled to 10° C. Then stirred for 10 minutes at 10-15° C. and the separated solid is filtered, washed with diisopropyl ether (15 ml) and dried at 50-55° C. for 2 hours to give 2gm of amorphous gemifloxacin free base (HPLC Purity: 99.8%).

EXAMPLE 4

Gemifloxacin free base (3 gm) is added to methylene dichloride (65 ml) at 25-30° C., ethanol (20 ml) is added to form a clear solution. To the solution, lactic acid (0.6ml) is added at 25-30° C., stirred for 1 hour and then cooled to 10° C. Filtered the solid and dried at 50-1 55° C. to give 3 gm of gemifloxacin lactate (HPLC Purity: 99.93%).

EXAMPLE 5

Gemifloxacin free base (3 gm) is added to methylene dichloride (65 ml) at 25-30 ° C., ethanol (20 ml) is added to form a clear solution. To the solution, formic acid (0.4ml) is added at 25-1 30° C., stirred for 1 hour and then cooled to 10° C. Filtered the solid and dried at 50- 55° C. to give 2.6 gm of gemifloxacin formate (HPLC Purity: 99.93%).

EXAMPLE 6

The wet gemifloxacin (2 gm obtained in example 1) is dried under vacuum at 50-55 ° C. until the water content is reduced to 2.0% to obtain gemifloxacin hemihydrate (HPLC Purity: 99.92%).

EXAMPLE 7

The wet gemifloxacin (2 gm obtained in example 1) is dried under vacuum at 50-55 ° C. until the water content is reduced to 4.8% to obtain gemifloxacin monohydrate (HPLC Purity: 99.90%).

EXAMPLE 8

The wet gemifloxacin (2 gm obtained in example 1) is dried under vacuum at 50 -55 ° C. until the water content is reduced to 6.1% to obtain gemifloxacin sesquihydrate (HPLC Purity: 99.93%).

EXAMPLE 9

The composition of a gemifloxacin infusion solution is as follows.

| Formulation | Composition |
| --- | --- |
| Gemifloxacin | 70 mg |
| Lactic acid 20% (w/w) | 144.3 mg |
| Hydrochloric acid | 1.5 mg |
| Sodium chloride | 5.4 gm |
| Water | 600.0 ml |
| pH | approx. 4.3 |
| Osm: | approx. 0.29 Osm/kg |

We claim:
1. Gemifloxacin hemihydrate.
2. A process for the preparation of gemifloxacin hemihydrate of claim 1, which comprises drying wet gemifloxacin at 40-100° C. until the water content is reduced to 1.8-2.4% by weight.
3. The process according to claim 2, wherein the drying is carried out at 50-70° C.
4. A pharmaceutical composition comprising gemifloxacin hemihydrate and a pharmaceutically acceptable excipient.

* * * * *